United States Patent [19]
de la Mettrie et al.

[11] Patent Number: 6,010,541
[45] Date of Patent: Jan. 4, 2000

[54] OXIDATION DYE COMPOSITION FOR KERATIN FIBERS COMPRISING A NONIONIC AMPHIPHILIC POLYMER

[75] Inventors: Roland de la Mettrie, Le Vesinet; Françoise Boudy, Paris, both of France

[73] Assignee: L'Oreal, Paris, France

[21] Appl. No.: 08/875,469

[22] PCT Filed: Jul. 10, 1997

[86] PCT No.: PCT/FR97/01262

§ 371 Date: Mar. 6, 1998

§ 102(e) Date: Mar. 6, 1998

[87] PCT Pub. No.: WO98/03150

PCT Pub. Date: Jan. 29, 1998

[30] Foreign Application Priority Data

Jul. 23, 1996 [FR] France ............... 96 09253

[51] Int. Cl.$^7$ ............... A61K 7/13
[52] U.S. Cl. ............... 8/412; 8/406; 8/407; 8/408; 8/410; 8/421; 8/424; 8/552
[58] Field of Search ............... 8/406, 407, 408, 8/409, 410, 411, 412, 429, 431, 435, 552, 553, 561, 562, 421, 424; 424/70.11, 70.13, 70.15, 70.16, 70.17

[56] References Cited

U.S. PATENT DOCUMENTS

| | | | |
|---|---|---|---|
| Re. 33,786 | 1/1992 | Pohl et al. | 8/406 |
| 3,200,040 | 8/1965 | Lange | 546/264 |
| 3,530,215 | 9/1970 | Greif et al. | 424/70.16 |
| 3,973,901 | 8/1976 | Micchelli et al. | 8/425 |
| 3,990,991 | 11/1976 | Gerstein | 501/84 |
| 4,003,699 | 1/1977 | Rose et al. | 8/10.2 |
| 4,217,914 | 8/1980 | Jacquet et al. | 8/426 |
| 4,240,450 | 12/1980 | Grollier et al. | 8/406 |
| 4,283,384 | 8/1981 | Jacquet et al. | 8/406 |
| 4,445,521 | 5/1984 | Grollier et al. | 8/406 |
| 4,496,708 | 1/1985 | Dehm et al. | 528/76 |
| 4,526,781 | 7/1985 | Goldberg et al. | 424/70.21 |
| 4,530,830 | 7/1985 | McKaba et al. | 424/70.2 |
| 4,567,038 | 1/1986 | Ciaudelli et al. | 424/59 |
| 4,567,039 | 1/1986 | Stadnick et al. | 132/70 |
| 4,714,610 | 12/1987 | Gerstein | 424/70.27 |
| 4,776,855 | 10/1988 | Pohl et al. | 8/406 |
| 4,839,166 | 6/1989 | Grollier et al. | 424/70.13 |
| 4,904,275 | 2/1990 | Grollier | 8/406 |
| 4,927,627 | 5/1990 | Schrader et al. | 8/406 |
| 4,973,475 | 11/1990 | Schnetzinger et al. | 424/70.5 |
| 4,986,983 | 1/1991 | Gerstein | 424/70.21 |
| 5,061,289 | 10/1991 | Clausen et al. | 8/405 |
| 5,071,441 | 12/1991 | Schnetzinger et al. | 8/405 |
| 5,100,658 | 3/1992 | Bolich, Jr. et al. | 8/405 |
| 5,106,609 | 4/1992 | Bolich, Jr. et al. | 8/405 |
| 5,163,010 | 11/1992 | Klein et al. | 364/479 |
| 5,277,899 | 1/1994 | McCall | 424/70.19 |
| 5,281,654 | 1/1994 | Eisenhart et al. | 524/500 |
| 5,290,555 | 3/1994 | Guthauser et al. | 424/401 |
| 5,304,370 | 4/1994 | Hawkins et al. | 132/205 |
| 5,306,489 | 4/1994 | Goldberg et al. | 424/70.14 |
| 5,374,420 | 12/1994 | Gerstein | 424/70.11 |
| 5,376,146 | 12/1994 | Casperson et al. | 8/408 |
| 5,380,340 | 1/1995 | Neunhoeffer et al. | 8/409 |
| 5,389,363 | 2/1995 | Snyder et al. | 424/70.7 |
| 5,391,368 | 2/1995 | Gerstein | 424/70.13 |
| 5,393,305 | 2/1995 | Cohen et al. | 8/406 |
| 5,443,855 | 8/1995 | Wolf et al. | 424/401 |
| 5,478,562 | 12/1995 | Cauwet et al. | 424/401 |
| 5,519,063 | 5/1996 | Mondet et al. | 514/772.4 |
| 5,534,267 | 7/1996 | Neunhoeffer et al. | 424/701 |
| 5,609,651 | 3/1997 | Mager et al. | 8/406 |
| 5,663,366 | 9/1997 | Neunhoffer et al. | 548/371.4 |
| 5,700,456 | 12/1997 | Dubief et al. | 424/70.17 |
| 5,807,545 | 9/1998 | Coffindaffer et al. | 424/70.11 |

FOREIGN PATENT DOCUMENTS

| | | |
|---|---|---|
| 133 905 | 3/1985 | European Pat. Off. . |
| 167 866 | 1/1986 | European Pat. Off. . |
| 168 719 | 1/1986 | European Pat. Off. . |
| 0 241 707 | 10/1987 | European Pat. Off. . |
| 0 412 705 | 2/1991 | European Pat. Off. . |
| 0 412 706 | 2/1991 | European Pat. Off. . |
| 0 412 710 | 2/1991 | European Pat. Off. . |
| 533 408 | 3/1993 | European Pat. Off. . |
| 0 555 155 | 8/1993 | European Pat. Off. . |
| 216 479 | 8/1994 | European Pat. Off. . |
| 673 641 | 9/1995 | European Pat. Off. . |
| 0 875 237 | 11/1998 | European Pat. Off. . |
| 2 327 761 | 10/1976 | France . |
| 2 446 633 | 1/1979 | France . |
| 2 679 444 | 1/1993 | France . |

(List continued on next page.)

OTHER PUBLICATIONS

PCT Search Report for WO 98/03150, Jan. 1998.
R&H Provisional Application 60/045390 filed May 2, 1997.
Ingredients for Personal Care, Product Information, Thickeners and Rheology Modifiers Elfacos® T 211 and Elfacos® T 212. (3 pages), Jul. 1998.
Aculyn® 44 thickener/stabilizer information (6 pages), 1992 (no month available).
English Language Abstract of EP 0 673 641, L'Oreal, Sep. 1995.
English Language Abstract of JP 88–169571, Kao Corp., Jul. 1988.
English Language Abstract of JP 91–333495, Kao Corp., Dec. 1991.
May 27 (27 mai), 1994 letter from D. Boutet of Akzo Nobel to M. Maes of L'Oréal.

*Primary Examiner*—Caroline D. Liott
*Attorney, Agent, or Firm*—Finnegan, Henderson, Farabow, Garrett & Dunner, L.L.P.

[57] ABSTRACT

An oxidation dye composition for keratin fiberes, and in particular for human keratin fibers such as the hair, comprising, in a medium which is suitable for dyeing, at least one oxidation dye precursor and optionally one or more couplers, characterized in that it also comprises a nonionic amphiphilic polymer containing at least one fatty chain and at least one hydrophilic unit, and the invention also relates to the processes and dyeing devices using the said oxidation dye composition.

55 Claims, No Drawings

FOREIGN PATENT DOCUMENTS

| | | |
|---|---|---|
| 6-247833 | 9/1994 | Japan . |
| 1026978 | 3/1963 | United Kingdom . |
| 1153196 | 6/1966 | United Kingdom . |
| 1066207 | 4/1967 | United Kingdom . |
| 1236560 | 6/1971 | United Kingdom . |
| 1257907 | 12/1971 | United Kingdom . |
| 2 124 081 | 2/1994 | United Kingdom . |
| WO 91/11985 | 8/1991 | WIPO . |
| WO 91/15186 | 10/1991 | WIPO . |
| WO 91/15187 | 10/1991 | WIPO . |
| WO 94/04125 | 3/1994 | WIPO . |
| WO 99/36047 | 7/1999 | WIPO . |

OXIDATION DYE COMPOSITION FOR KERATIN FIBERS COMPRISING A NONIONIC AMPHIPHILIC POLYMER

The present invention relates to a composition for the oxidation dyeing of keratin fibers, and in particular of human keratin fibers such as the hair, comprising at least one oxidation dye precursor and optionally one or more couplers and at least one non ionic amphiphilic polymer containing at least one fatty chain and at least one hydrophilic unit.

It is known to dye keratin fibers, and in particular human hair, with dye compositions containing oxidation dye precursors, which are generally known as "oxidation bases", in particular ortho- or para-phenylenediamines, ortho- or para-aminophenols and heterocyclic bases.

Oxidation dye precursors are compounds which are initially colourless or only slightly coloured and which develop their dyeing power on the hair in the presence of oxidizing agents, leading to the formation of coloured compounds. The formation of these coloured compounds results either from an oxidative condensation of the "oxidation bases" with themselves or from an oxidative condensation of the "oxidation bases" with colour-modifier compounds, or "couplers", which are generally present in the dye compositions used in oxidation dyeing and are represented more particularly by meta-phenylenediamines, meta-aminophenols and meta-diphenols and certain heterocyclic compounds.

The variety of molecules used, which consists, on the one hand, of "oxidation bases" and, on the other hand, of "couplers", makes it possible to obtain a wide variety of colours.

In order to localize the oxidation dye product on the hair when it is applied, in order for it not to run onto the face or outside the areas which it is proposed to dye, use has been made hitherto of traditional thickeners such as crosslinked polyacrylic acid, hydroxyethylcelluloses or waxes or alternatively mixtures of nonionic surfactants with an HLB (hydrophilic-lipophilic balance) which, when suitably selected, gives rise to the gelling effect when they are diluted with water and/or surfactants.

However, the Applicant has observed that the ingredients of the traditional thickener, surfactant and solvent type generally curb the rise of the dye on the fibers, which is reflected in a dull shade and also in a larger use of dye, of solvent and/or of surfactants in order to dissolve the dye, if it is nevertheless desired to obtain and intense shade.

Moreover, the Applicant has also observed that after mixing with the oxidant, dye compositions containing the oxidation dye precursor or precursors and optionally the coupler or couplers, and also the said ingredients, lose some of their gelled nature and consequently give rise to undesirable running.

After considerable research conducted in this matter, the Applicant has now discovered that it is possible to obtain oxidation dye compositions (after mixing with the oxidants) which do not run and thus remain better localized at the point of application, and which also make it possible to obtain more intense or more chromatic (more luminous) shades, if an effective amount of a nonionic amphiphilic polymer containing at least one fatty chain and at least one hydrophilic unit is introduced (i) either into the composition containing the oxidation dye precursor or precursors and optionally the coupler or couplers (or composition (A)), or (ii) into the oxidizing compositions (or composition (B)), or (iii) into both compositions at once.

For the purposes of the present invention, the chromaticity (luminosity) is defined by the value c* in the L*, a*, b* colorimetric notation system of the Commission Internationale de l'Eclairage (C.I.E.) This value is equal to the square route of the sum $a^2+b^2$ (+a is red, −a is green, +b is yellow, −b is blue). The shade is proportionately more luminous the greater the value of c*.

In this notation system, L* defines the intensity of the shade. The shade is proportionately more intense the lower the value of L* (0=black, 100=white).

These discoveries form the basis of the present invention.

The subject of the present invention is thus a composition for the oxidation dyeing of keratin fibers, in particular human keratin fibers such as the hair, of the type comprising, in a medium which is suitable for dyeing, at least one oxidation dye precursor (oxidation base) and, where appropriate, one or more couplers, which is characterized in that it also contains at least one nonionic amphiphilic polymer containing at least one fatty chain and at least one hydrophilic unit, with the proviso that the nonionic amphiphilic polymer is other than:

(a) a copolymer of polyethylene glycol (containing 20 EO) ether of stearyl alcohol and of one or more lower acrylic acid esters and/or lower methacrylic acid esters, (b) a copolymer of polyalkylene glycol ether of $C_{16}$–$C_{22}$ alcohol and of one or more esters of $C_{16}$–$C_{22}$ carboxylic acid.

By means of the present invention, it is also possible, advantageously, to reduce the consumption of surfactants, or even to dispense with them altogether.

The invention also makes it possible to decrease the amount of active dyestuffs used in the dye compositions, when compared with the standard techniques known in the prior art.

Another subject of the present invention relates to a ready-to-use composition for dyeing keratin fibers, which contains at least one oxidation dye precursor and optionally at least one coupler, and at least one nonionic amphiphilic polymer containing at least one fatty chain and at least one hydrophilic unit as defined above, and an oxidizing agent.

The invention is also directed towards a process for dyeing keratin fibers, and in particular human keratin fibers such as the hair, which consists in applying to these fibers at least one composition (A1) containing, in a medium which is suitable for dyeing, at least one oxidation dye precursor and optionally at least one coupler, in combination with at least one nonionic amphiphilic polymer containing at least one fatty chain and at least one hydrophilic unit as defined above, the colour being developed at alkaline, neutral or acidic pH using an oxidizing agent which is mixed with the composition (A1) only at the time of use or which is present in a composition (B1) that is applied sequentially without intermediate rinsing.

The invention is also directed towards a variant of this process, which consists in applying to the fibers at least one composition (A2) containing, in a medium which is suitable for dyeing, at least one oxidation dye precursor and optionally at least one coupler, in the presence or absence of nonionic amphiphilic polymer containing at least one fatty chain and at least one hydrophilic unit as defined above, the colour being developed at alkaline, neutral or acidic pH using an oxidizing composition (B2) which contains an oxidizing agent and an effective amount of at least one nonionic amphiphilic polymer containing at least one fatty chain and at least one hydrophilic unit as defined above, and which is mixed with the composition (A2) only at the time of use or which is applied sequentially without intermediate rinsing.

The subject of the invention is also multi-compartment "kits" or devices for dyeing, a first compartment of which contains at least one oxidation dye precursor, optionally at least one coupler and at least one nonionic amphiphilic polymer containing at least one fatty chain and at least one hydrophilic unit as defined above, and a second compartment of which contains an oxidizing agent.

According to another variant, the subject of the invention is also multi-compartment kits or devices for dyeing, a first compartment of which contains at least one oxidation dye precursor, optionally at least one coupler, in the presence or absence of nonionic amphiphilic polymer containing at least one fatty chain and at least one hydrophilic unit as defined above, and a second compartment of which contains an oxidizing agent and an effective amount of at least one nonionic amphiphilic polymer containing at least one fatty chain and at least one hydrophilic unit as defined above.

The invention also relates to the use of the oxidation dyeing composition defined above or to the use of a multi-compartment kit or device for dyeing as defined above for dyeing human keratin fibers such as the hair.

However, other characteristics, aspects, objects and advantages of the invention will become even more apparent on reading the description and the examples which follow.

The nonionic amphiphilic polymers containing at least one fatty chain and at least one hydrophilic unit, which are used according to the invention, are preferably chosen from:
(1) celluloses modified with groups containing at least one fatty chain; mention may be made, for example, of:
   hydroxyethyl celluloses modified with groups containing at least one fatty chain such as alkyl, arylalkyl or alkylaryl groups or mixtures thereof, and in which the alkyl groups are preferably $C_8$–$C_{22}$, such as the product Natrosol Plus Grade 330 CS ($C_{16}$ alkyls) sold by the company Aqualon, or the product Bermocoll EHM 100 sold by the company Berol Nobel,
   those modified with polyalkylene glycol alkylphenyl ether groups, such as the product Amercell Polymer HM-1500 (polyethylene glycol (15) nonylphenyl ether) sold by the company Amerchol.
(2) hydroxypropyl guars modified with groups containing at least one fatty chain, such as the product Esaflor HM 22 ($C_{22}$ alkyl chain) sold by the company Lamberti, and the products Miracare $XC_{95}$-3 ($C_{14}$ alkyl chain) and RE205-1 ($C_{20}$ alkyl chain) sold by the company Rhône-Poulenc.
(3) polyether urethanes containing at least one fatty chain such as $C_8$–$C_{30}$ alkyl or alkenyl groups, for instance the products Dapral T210 and Dapral T212, now known respectively as Elfacos T210 and Elfacos T212, sold by the company Akzo Nobel.
(4) copolymers of vinylpyrrolidone and of hydrophobic monomers containing a fatty chain; mention may be made, for example, of:
   the products Antaron V216 or Ganex V216 (vinylpyrrolidone/hexadecene copolymer) sold by the company ISP
   the products Antaron V220 or Ganex V220 (vinylpyrrolidone/eicosene copolymer) sold by the company ISP.
(5) copolymers of $C_1$–$C_6$ alkyl methacrylates or acrylates and of amphiphilic monomers containing at least one fatty chain, such as, for example, the oxyethylenated methyl methacrylate/stearyl acrylate copolymer sold by the company Goldschmidt under the name Antil 208.
(6) copolymers of hydrophilic methacrylates or acrylates and of hydrophobic monomers containing at least one fatty chain, such as, for example, the polyethylene glycol methacrylate/lauryl methacrylate copolymer.

The nonionic amphiphilic polymers containing at least one fatty chain and at least one hydrophilic unit according to the invention are preferably used in an amount which may range approximately from 0.05 to 10% by weight relative to the total weight of the dye composition applied to the fibers. More preferably, this amount varies approximately from 0.2 to 5% by weight.

The oxidation dye precursors which may be used in the context of the present invention are chosen from those conventionally known in oxidation dyeing, and among which mention may be made in particular of:
para-phenylenediamines of formula (I) below, and the addition salts thereof with an acid:

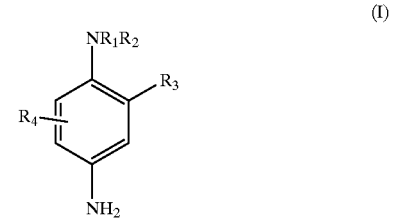

in which:
R$_1$ represents a hydrogen atom or a $C_1$–$C_4$ alkyl, $C_1$–$C_4$ monohydroxyalkyl, $C_2$–$C_4$ polyhydroxyalkyl or 4'-aminophenyl radical,
R$_2$ represents a hydrogen atom or a $C_1$–$C_4$ alkyl, $C_1$–$C_4$-monohydroxyalkyl or $C_2$–$C_4$ polyhydroxyalkyl radical,
R$_3$ represents a hydrogen atom, a halogen atom such as a chlorine atom, or a $C_1$–$C_4$ alkyl, sulpho, carboxyl, $C_1$–$C_4$ monohydroxyalkyl or $C_1$–$C_4$ hydroxyalkoxy radical,
R$_4$ represents a hydrogen atom or a $C_1$–$C_4$ alkyl radical.

Among the para-phenylenediamines of formula (I) above, mention may be made more particularly of para-phenylenediamine, para-toluylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methyl-aniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxy-ethyl)aniline, 2-β-hydroxyethyl-para-phenylenediamine, 2-fluoro-para-phenylenediamine, 2-isopropyl-para-phenylenediamine, N-(β-hydroxypropyl)-para-phenylene-diamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylene-diamine, and the addition salts thereof with an acid.

Among the para-phenylenediamines of formula (I) above, para-phenylenediamine, para-toluylene-diamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid are most particularly preferred.

the bis(phenyl)alkylenediamines corresponding to formula (II) below, and the addition salts thereof with an acid:

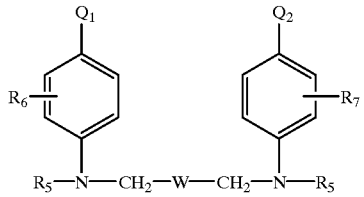
(II)

in which:
Q$_1$ and Q$_2$, which may be identical or different, represent a hydroxyl radical or a radical NHR$_8$ in which R$_8$ represents a hydrogen atom or a C$_1$–C$_4$ alkyl radical, R$_5$ represents a hydrogen atom, a C$_1$–C$_4$ alkyl, C$_1$–C$_4$ monohydroxyalkyl or C$_2$–C$_4$ polyhydroxy alkyl radical or a C$_1$–C$_4$ aminoalkyl radical in which the amino residue may be substituted, R$_6$ and R$_7$, which may be identical or different, represent a hydrogen or halogen atom or a C$_1$–C$_4$ alkyl radical, W represents a radical taken from the group consisting of the following radicals:

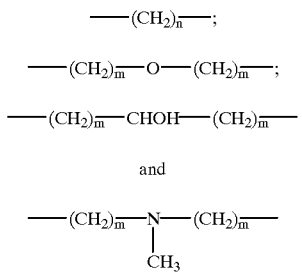

in which n is an integer between 0 and 8 inclusive and m is an integer between 0 and 4 inclusive.

Among the bis(phenyl)alkylenediamines of formula (II) above, mention may be made more particularly of N,N'-bis(β-hydroxyethyl)-N,N'-bis(4'-aminophenyl)-1,3-diamino-2-propanol, N,N'-bis(β-hydroxyethyl)-N,N'-bis-(4'-aminophenyl)ethylene-diamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof with an acid.

Among these bis(phenyl)alkylenediamines of formula (II), N,N'-bis(β-hydroxyethyl)-N,N'-bis(4'-aminophenyl)-1,3-diamino-2-propanol or one of the addition salts thereof with an acid is particularly preferred.

the para-aminophenols corresponding to formula (III) below, and the addition salts thereof with an acid:

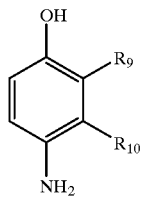
(III)

in which
R$_9$ represents a hydrogen atom or a C$_1$–C$_4$ alkyl, C$_1$–C$_4$ monohydroxyalkyl, (C$_1$–C$_4$)alkoxy(C$_1$–C$_4$)alkyl, C$_1$–C$_4$ aminoalkyl or hydroxy(C$_1$–C$_4$)alkyl amino (C$_1$–C$_4$)alkyl radical, R$_{10}$ represents a hydrogen or fluorine atom or a C$_1$–C$_4$ alkyl, C$_1$–C$_4$ monohydroxyalkyl, C$_2$–C$_4$ polyhydroxy-alkyl, C$_1$–C$_4$ aminoalkyl, C$_1$–C$_4$ cyanoalkyl or (C$_1$–C$_4$)alkoxy(C$_1$–C$_4$)alkyl radical, it being understood that at least one of the radicals R$_9$ or R$_{10}$ represents a hydrogen atom.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

the ortho-aminophenols which may be used as oxidation bases in the context of the present invention are chosen in particular from 2-aminophenol, 2-amino-1-hydroxy-5-methylbenzene, 2-amino-1-hydroxy-6-methylbenzene and 5-acetamido-2-aminophenol, and the addition salts thereof with an acid.

the heterocyclic bases which may be used as oxidation bases in the context of the present invention are chosen in particular from pyridine derivatives, pyrimidine derivatives and pyrazole derivatives, and the addition salts thereof with an acid.

Among the pyridine derivatives, mention may be made more particularly of the compounds described, for example, in patents GB-1,026,978 and GB-1,153,196, such as 2,5-diaminopyridine, and the addition salts thereof with an acid.

Among the pyrimidine derivatives, mention may be made more particularly of the compounds described, for example, in German patent DE-2,359,399 or Japanese patents JP-88-169,571 and JP-91-333,495, such as 2,4,5,6-tetraaminopyrimidine and 4-hydroxy-2,5,6-triaminopyrimidine, and the addition salts thereof with an acid.

Among the pyrazole derivatives, mention may be made more particularly of compounds described in patents DE-3,843,892 and DE-4,133,957 and patent applications WO-94/08969 and WO-94/08970, such as 4,5-diamino-1-methylpyrazole, 3,4-diaminopyrazole and 4,5-diamino-1-(4'-chlorobenzyl)pyrazole, and the addition salts thereof with an acid.

According to the invention, the oxidation base or bases preferably represent from 0.0005 to 12% by weight approximately relative to the total weight of the composition (A) and even more preferably from 0.005 to 6% by weight approximately.

The couplers which may be used in the dyeing process according to the invention are those conventionally used in oxidation dye compositions, that is to say meta-phenylenediamines, meta-aminophenols and meta-diphenols, mono- or polyhydroxynaphthalene derivatives, sesamol and derivatives thereof and heterocyclic compounds such as, for example, indole couplers, indoline couplers and pyridine couplers, and the addition salts thereof with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the composition (A) and even more preferably from 0.005 to 5% by weight approximately.

In general, the addition salts with an acid of the oxidation bases and couplers are chosen in particular from the hydrochlorides, hydrobromides, sulphates, tartrates, lactates and acetates.

The composition (A) may also contain, in addition to the oxidation dye precursors defined above and the optional associated couplers, direct dyes in order to enrich the shades with glints. These direct dyes may be chosen in particular from nitro dyes, azo dyes or anthraquinone dyes.

The composition (A) and/or the composition (B) may also more particularly contain at least one cationic or amphoteric substantive polymer as defined on pages 3 and 4 of patent application EP-0,673,641 A1, and of which it is advantageously preferred to use:

the quaternary polyammonium polymers prepared and described in French patent 2,270,846, consisting of repeating units corresponding to formula (IV) below:

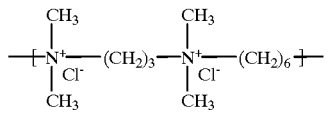

(IV)

and the molecular weight of which, determined by gel permeation chromatography, is between 9500 and 9900;

the quaternary polyammonium polymers prepared and described in French patent 2,270,846, consisting of repeating units corresponding to formula (V) below:

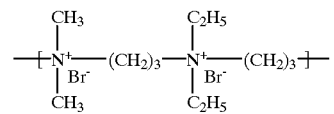

(V)

and the molecular weight of which, determined by gel permeation chromatography, is about 1200.

The medium for composition (A) which is suitable for dyeing is preferably an aqueous medium consisting of water and may optionally contain cosmetically acceptable organic solvents including, more particularly, alcohols such as ethyl alcohol, isopropyl alcohol, benzyl alcohol or phenylethyl alcohol, or glycols or glycol ethers such as, for example, ethylene glycol monomethyl, monoethyl and monobutyl ethers, propylene glycol or ethers thereof such as, for example, propylene glycol monomethyl ether, butylene glycol, dipropylene glycol and diethylene glycol alkyl ethers such as, for example, diethylene glycol monoethyl ether or monobutyl ether, in concentrations of approximately between 0.5 and 20% and, preferably, approximately between 2 and 10% by weight relative to the total weight of the composition.

The composition (A) may also contain an effective amount of other agents, which are moreover previously known in oxidation dyeing, such as various common adjuvants, for instance sequestering agents, hair conditioners, silicones, preserving agents, opacifiers, etc., and optionally anionic, cationic, nonionic, amphoteric or zwitterionic surfactants or imixtures thereof.

The said composition may also contain antioxidants. These may be chosen in particular from sodium sulphite, thioglycolic acid, thiolactic acid, sodium bisulphite, dehydroasorbic acid, hydroquinone, 2-methylhydroquinone, tert-butylhydroquinone and homogentisic acid, and they are then generally present in amounts ranging approximately from 0.05 to 1.5% by weight relative to the total weight of the composition.

Obviously, a person skilled in the art will take care to select the optional complementary compound or compounds mentioned above such that the advantageous properties intrinsically associated with the dye composition according to the invention are not, or are not substantially, adversely affected by the addition or additions envisaged.

In the composition (B), the oxidizing agent is preferably chosen from urea peroxide, alkali metal bromates or ferricyanides, and persalts such as perborates and persulphates. The use of hydrogen peroxide is particularly preferred.

The composition (B) advantageously consists of an aqueous hydrogen peroxide solution whose titre may range, more particularly, approximately from 2.5 to 40 volumes and, even more preferably, approximately from 5 to 20 volumes.

The pH of the ready-to-use composition applied to the keratin fibers (composition resulting from mixing together the dye composition (A) and the oxidizing composition (B)) is generally between the values 4 and 11. It is preferably between 6 and 10, and may be adjusted to the desired value by means of acidifying or basifying agents that are well known in the state of the art in the dyeing of keratin fibers.

Among the basifying agents which may be mentioned, by way of example, are aqueous ammonia, alkali metal carbonates, alkanolamines such as mono-, di- and triethanolamines and derivatives thereof, sodium hydroxide, potassium hydroxide and the compounds of formula (VI) below:

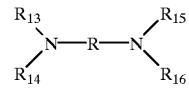

(VI)

in which R is a propylene residue optionally substituted with a hydroxyl group or a $C_1$–$C_4$ alkyl radical; $R_{13}$, $R_{14}$, $R_{15}$ and $R_{16}$, which may be identical or different, represent a hydrogen atom or a $C_1$–$C_4$ alkyl or $C_1$–$C_4$ hydroxyalkyl radical.

The acidifying agents are conventionally, by way of example, inorganic or organic acids such as hydrochloric acid, orthophosphoric acid, carboxylic acids such as tartaric acid, citric acid or lactic acid, or sulphonic acids.

The dyeing process according to the invention 1preferably consists in applying a mixture, which is prepared as required at the time of use from the compositions (A) and (B) described above, onto the dry or wet keratin fibers and in leaving the mixture to act for an exposure period preferably ranging from 1 to 60 minutes approximately, and more preferably from 10 to 45 minutes approximately, in rinsing the fibers, then in optionally washing them with shampoo and then rinsing them again and drying them.

Concrete examples illustrating the invention will now be given without, however, being limiting in nature.

EXAMPLE 1

The following dye composition, in accordance with the invention, was prepared:

| | | |
|---|---|---|
| NATROSOL PLUS GRADE 330 CS (Aqualon) | | 1.0 g |
| Oleic acid | | 3.0 g |
| Aqueous sodium bisulphite solution containing 35% AM* | | 0.45 g AM* |
| Para-phenylenediamine | | 0.162 g |
| Resorcinol | | 0.165 g |
| Aqueous amnnonia (20% $NH_3$) | | 11.5 g |
| Sequestering agent | q.s | |
| Water | q.s.p | 100 g |

AM* = active material

At the time of use, this composition was mixed weight for weight with a 20-volumes aqueous hydrogen peroxide solution and the mixture obtained was then applied to locks of permanent-waved hair containing 90% white hairs. After leaving to stand on the locks for 30 minutes, they were rinsed and then washed with a shampoo, rinsed again and then dried.

Using an I.C.S. spectrocolorimeter, the value L* in the L*, a*, b* international colour notation system from C.I.E. was measured.

The result was as follows: L*=32.19

COMPARATIVE EXAMPLE 2

Example 1 was repeated, replacing 1 gram of nonionic amphiphilic polymer (Natrosol Plus Grade 330 CS) by th e mixture of the following two nonionic surfactants (allowing the same viscosity to be obtained):

24 grams of decyl alcohol ($C_{10}$-$C_{12}$-$C_{14}$/85-8.5–6.5) oxyethylenated with 3.5 mol of ethylene oxide, sold under the name Mergital BL 309 by the company Henkel, and 16 grams of decyl alcohol ($C_{10}$-$C_{12}$-$C_{14}$/85-8.5–6.5) oxyethylenated with 5.5 mol of ethylene oxide, sold under the name Mergital BL 589 by the company Henkel.

The same procedure as in Example 1 was then followed. The result was as follows: L*=35.72

Conclusion: the shade obtained according to the invention is more intense (lower L*) than that obtained according to the prior art.

We claim:

1. A composition for the oxidation dyeing of keratin fibers comprising:
   at least one oxidation dye precursor, and
   at least one nonionic amphiphilic polymer comprising at least one fatty chain and at least one hydrophilic unit selected from polyether urethanes comprising at least one fatty chain.

2. A composition according to claim 1 wherein said keratin fibers are human keratin fibers.

3. A composition according to claim 2 wherein said human keratin fibers are hair and wherein said composition further contains a medium suitable for dyeing.

4. A composition according to claim 3 wherein said at least one nonionic amphiphilic polymer is a polyether urethane comprising at least one fatty chain selected from $C_8$–$C_{30}$ alkyl groups and $C_8$–$C_{30}$ alkenyl groups.

5. A composition according to claim 3 wherein said at least one oxidation dye precursor is selected from ortho- and para-phenylenediamines, bis(phenyl)alkylenediamines, ortho- and para-aminophenols, heterocyclic bases, and acid addition salts thereof.

6. A composition according to claim 3 wherein said at least one oxidation dye precursor is present in concentrations ranging from 0.0005 to 12% by weight relative to the total weight of the composition.

7. A composition according to claim 3 wherein said composition further contains at least one coupler.

8. A composition according to claim 7 wherein said at least one coupler is selected from meta-phenylenediamines, meta-aminophenols, meta-diphenols, mono- and polyhydroxynaphthalene couplers, heterocyclic couplers, and acid addition salts thereof.

9. A composition according to claim 7 wherein said at least one coupler is present in concentrations ranging from 0.0001 to 10% by weight relative to the total weight of the composition.

10. A composition according to claim 8 wherein said acid addition salts are seleocted from hydrochlorides, hydrobromides, sulphates, tartrates, lactates and acetates.

11. A composition according to claim 5 wherein said acid addition salts are selected from hydrochlorides, hydrobromides, sulphates, tartrates, lactates and acetates.

12. A composition according to claim 3 wherein said composition further comprises direct dyes.

13. A composition according to claim 3 wherein said composition further comprises at least one reducing agent present in an amount ranging from 0.05 to 3% by weight relative to the total weight of the composition.

14. A composition according to claim 3 wherein said composition further comprises an oxidizing agent.

15. A composition according to claim 14 wherein said composition has a pH ranging from 4 to 11.

16. A composition according to claim 14 wherein said oxidizing agent is selected from hydrogen peroxide, urea peroxide, alkali metal bromates, alkali metal ferricyanides, and persalts.

17. A composition according to claim 14 wherein said oxidizing agent is an aqueous hydrogen peroxide solution having a titre ranging from 2.5 to 40 volumes.

18. A composition according to claim 3 wherein said polyether urethanes comprising at least one fatty chain are present in an amount ranging from 0.05 to 10% by weight relative to the total weight of the composition to be applied to said hair for the oxidation dyeing of said hair.

19. A composition according to claim 12, wherein said polyether urethane comprising at least one fatty chain is present in an amount ranging from 0.2 to 5% by weight relative to the total weight of the composition to be applied to said hair for the oxidation dyeing of said hair.

20. A composition for the oxidation dyeing of keratin fibers comprising:
   a dye composition comprising:
      at least one oxidation dye precursor, and
      at least one nonionic amphiphilic polymer comprising at least one fatty chain and at least one hydrophilic unit selected from polyether urethanes comprising at least one fatty chain; and an oxidizing composition comprising an oxidizing agent.

21. A composition for the oxidation dyeing of keratin fibers comprising:
   a dye composition comprising:
      at least one oxidation dye precursor, and
      at least one nonionic amphiphilic polymer comprising at least one fatty chain and at least one hydrophilic unit selected from polyether urethanes comprising at least one fatty chain, and
   an oxidizing composition comprising an oxidizing agent, wherein said oxidizing composition further comprises at least one nonionic amphiphilic polymer comprising at least one fatty chain and at least one hydrophilic unit selected from polyether urethanes comprising at least one fatty chain.

22. A process for oxidation dyeing of keratin fibers comprising the steps of:
   applying to said fibers a composition for the oxidation dyeing of keratin fibers comprising:
      at least one oxidation dye precursor, and
      at least one nonionic amphiphilic polymer comprising at least one fatty chain and at least one hydrophilic unit selected from polyether urethanes comprising at least one fatty chain, and
   applying an oxidizing agent to said fibers under conditions sufficient to develop color.

23. A process according to claim 22 wherein said keratin fibers are human keratin fibers.

24. A process according to claim 23 wherein said human keratin fibers are hair.

25. A process according to claim 24 wherein said oxidizing agent and said composition for the oxidation dyeing of keratin fibers are combined and said combination is thereafter applied to said hair.

26. A process according to claim 24 wherein said composition for the oxidation dyeing of keratin fibers and said oxidizing agent are applied to said hair sequentially.

27. A process for oxidation dyeing of keratin fibers comprising the steps of:
   applying to said fibers at least one composition comprising, in a medium which is suitable for dyeing:
      at least one oxidation dye precursor, and
      at least one nonionic amphiphilic polymer comprising at least one fatty chain and at least one hydrophilic unit selected from polyether urethanes comprising at least one fatty chain, and
   applying an oxidizing composition comprising an oxidizing agent to said fibers in alkaline, neutral or acidic medium to develop color.

28. A process according to claim 27 wherein said keratin fibers are human keratin fibers.

29. A process according to claim 28 wherein said human keratin fibers are hair.

30. A multicompartment kit for dyeing keratin fibers comprising at least two compartments which are separate from one another,
   said first compartment comprising a composition for the oxidation dyeing of keratin fibers comprising:
      at least one oxidation dye precursor, and
      at least one nonionic amphiphilic polymer comprising at least one fatty chain and at least one hydrophilic unit selected from polyether urethanes comprising at least one fatty chain; and
   said second compartment comprising an oxidizing composition comprising an oxidizing agent.

31. A multicompartment kit according to claim 30 wherein said keratin fibers are human keratin fibers.

32. A multicompartment kit or device according to claim 31 wherein said human keratin fibers are hair.

33. A ready-to-use composition for oxidation dyeing of keratin fibers comprising: at least one oxidation dye precursor, at least one nonionic, amphiphilic polyether urethane comprising at least one fatty chain; and an oxidizing agent.

34. A ready-to-use composition according to claim 33 wherein said keratin fibers are human keratin fibers.

35. A ready-to-use composition according to claim 34 wherein said human keratin fibers are hair.

36. A ready-to-use composition for the oxidation dyeing of keratin fibers, said composition comprising water, sodium sulphite, at least one oxidation dye precursor, al least one coupler, at least one nonionic, amphiphilic polyether urethane comprising at least one fatty chain, and at least one oxidizing agent,
   wherein said at least one oxidation dye precursor is selected from para-phenylenediamine, para-aminophenol, and acid addition salts of N,N-bis($\beta$-hydroxyethyl)-para-phenylenediamine
   and wherein said at least one coupler is selected from 3-aminophenol, 1,3-dihydroxybenzene, 2-methyl-1,3-dihydroxybenzene, 2-methyl-5-aminophenol, and $\alpha$-naphthol,
   and further wherein said at least one oxidizing agent is hydrogen peroxide.

37. A multicompartment kit for dyeing human hair comprising at least two compartments which are separate from each other,
   said first compartment comprising a composition for the oxidation dyeing of keratin fibers comprising:
      water;
      sodium sulphite;
      at least one oxidation dye precursor selected from para-phenylenediamine, para-aminophenol, and acid addition salts of N,N-bis($\beta$-hydroxyethyl-para-phenylenediamine;
      at least one coupler selected from 3-aminophenol, 1,3-dihydroxybenzene, 2-methyl-1,3-dihydroxybenzene, 2-methyl-5-aminophenol, and $\alpha$-naphthol; and
      at least one nonionic, amphiphilic polyether urethane comprising at least one fatty chain; and
   said second compartment comprising an oxidizing composition comprising hydrogen peroxide and water.

38. A multicompartment kit for dyeing human hair according to claim 37, wherein
   said first compartment comprises at least one nonionic, amphiphilic polyether urethane comprising at least one fatty chain, water, sodium sulphite, para-phenylenediamine, N,N-bis($\beta$-hydroxyethyl)-para-phenylenediamine sulfate, 1,3-dihydroxybenzene, 2-methyl-1,3-dihydroxybenzene, 2-methyl-5-aminophenol, and $\alpha$-naphthol; and
   said second compartment comprises hydrogen peroxide and water.

39. A multicompartment kit for dyeing human hair according to claim 37, wherein
   said first compartment comprises at least one nonionic, amphiphilic polyether urethane comprising at least one fatty chain, water, sodium sulphite, para-phenylenediamine, p-aminophenol, N,N-bis($\beta$- hydroxyethyl)-para-phenylenediamine sulfate, 2-methyl-1,3-dihydroxybenzene, 2-methyl-5-aminophenol, and α-naphthol; and said second compartment comprises hydrogen peroxide and water.

40. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, 1,3-dihydroxybenzene, 2-methyl-1,3-dihydroxybenzene, 2-methyl-5-aminophenol, 3-aminophenol, and α-naphthol; and said second compartment comprises hydrogen peroxide and water.

41. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, 1,3-dihydroxybenzene, 2-methyl-1,3-dihydroxybenzene, 2-methyl-5-aminophenol, and 3-aminophenol; and said second compartment comprises hydrogen peroxide and water.

42. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, 1,3-dihydroxybenzene, 2-methyl-1,3-dihydroxybenzene, 2-methyl-5-aminophenol, and α-naphthol; and said second compartment comprises hydrogen peroxide and water.

43. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, 1,3-dihydroxybenzene, 2-methyl-5-aminophenol, 3-aminophenol, and α-naphthol; and said second compartment comprises hydrogen peroxide and water.

44. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, 1,3-dihydroxybenzene, 2-methyl-5-aminophenol, and 3-aminophenol; and said second compartment comprises hydrogen peroxide and water.

45. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, 1,3-dihydroxybenzene, and 2-methyl-5-aminophenol; and said second compartment comprises hydrogen peroxide and water.

46. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, 2-methyl-5-aminophenol, and α-naphthol; and said second compartment comprises hydrogen peroxide and water.

47. A multicompartment kit for dyeing human hair according to claim 37, wherein said first compartment comprises at least one nonionic, amphiphilic polyether urethane comprising at least one fatty chain, water, sodium sulphite, para-phenylenediamine, N,N-bis(β-hydroxyethyl)-para-phenylenediamine sulfate, 1,3-dihydroxybenzene, and 3-aminophenol; and said second compartment comprises hydrogen peroxide and water.

48. A multicompartment kit for dyeing human hair according to claim 37, wherein said first compartment comprises at least one nonionic, amphiphilic polyether urethane comprising at least one fatty chain, water, sodium sulphite, para-phenylenediamine, N,N-bis(β-hydroxyethyl)-para-phenylenediamine sulfate, 1,3-dihydroxybenzene, and α-naphthol; and said second compartment comprises hydrogen peroxide and water.

49. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, N,N-bis(β-hydroxyethyl)-para-phenylenediamine sulfate, 1,3-dihydroxybenzene, 3-aminophenol, and α-naphthol; and said second compartment comprises hydrogen peroxide and water.

50. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, 1,3-dihydroxybenzene, 3-aminophenol, and α-naphthol; and said second compartment comprises hydrogen peroxide and water.

51. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, 1,3-dihydroxybenzene, and 3-aminophenol; and said second compartment comprises hydrogen peroxide and water.

52. A multicompartment kit for dyeing human hair according to claim 37, wherein said first compartment comprises at least one nonionic, amphiphilic polyether urethane comprising at least one fatty chain, water, sodium sulfite, para-phenylenediamine, p-aminophenol and 2-methyl-5-aminophenol; and said second compartment comprises hydrogen peroxide and water.

53. A multicompartment kit for dyeing human hair according to claim 37, wherein said first compartment comprises at least one nonionic, amphiphilic polyether urethane comprising at least one fatty chain, water, sodium sulphite, para-phenylenediamine, 3-aminophenol, N,N-bis(β-hydroxyethyl)-para-phenylenediamine sulfate, 1,3-dihydroxybenzene, and α-naphthol; and said second compartment comprises hydrogen peroxide and water.

54. A multicompartment kit for dyeing human hair according to claim 37, wherein said first compartment comprises at least one nonionic, amphiphilic polyether urethane comprising at least one fatty chain, water, sodium sulphite, para-phenylenediamine, 3-aminophenol, p-aminophenol, N,N-bis(β-hydroxyethyl)-para-phenylenediamine sulfate, 1,3-dihydroxybenzene, and 2-methyl-1,3-dihydroxybenzene; and said second compartment comprises hydrogen peroxide and water.

55. A multicompartment kit for dyeing human hair according to claim 37, wherein said first compartment comprises at least one nonionic, amphiphilic polyether urethane comprising at least one fatty chain, water, sodium sulphite, para-phenylenediamine, p-aminophenol, N,N-bis(β-hydroxyethyl)-para-phenylenediamine sulfate, 1,3-dihydroxybenzene, and 2-methyl-5-aminophenol; and said second compartment comprises hydrogen peroxide and water.

* * * * *

UNITED STATES PATENT AND TRADEMARK OFFICE
CERTIFICATE OF CORRECTION

PATENT NO. : 6,010,541
DATED : January 4, 2000
INVENTOR(S) : de la Mettrie et al.

It is certified that error appears in the above-indentified patent and that said Letters Patent is hereby corrected as shown below:

In claim 36, col. 12, line 16, replace "al" with --at--.

Signed and Sealed this

Sixth Day of March, 2001

Attest:

NICHOLAS P. GODICI

Attesting Officer     Acting Director of the United States Patent and Trademark Office